United States Patent
Nagel et al.

[11] Patent Number: 6,121,280
[45] Date of Patent: Sep. 19, 2000

[54] AZABICYCLIC ROTOMASE INHIBITORS

[75] Inventors: Arthur A. Nagel, Gales Ferry; James F. Blake, Mystic, both of Conn.

[73] Assignee: Pfizer Inc., New York, N.Y.

[21] Appl. No.: 09/255,242

[22] Filed: Feb. 22, 1999

Related U.S. Application Data

[60] Provisional application No. 60/079,138, Mar. 24, 1998.

[51] Int. Cl.⁷ .......................... A61K 31/44; C07D 221/02
[52] U.S. Cl. ............................ 514/299; 546/112
[58] Field of Search ..................... 546/200, 205, 546/207, 112; 514/299

[56] References Cited

U.S. PATENT DOCUMENTS 4,405,787  9/1983  Gaitanopoulos et al. .

FOREIGN PATENT DOCUMENTS

| 0113880 A2 | 7/1984 | European Pat. Off. . |
| 3246757 | 6/1984 | Germany . |
| 96/40140 | 12/1996 | WIPO . |
| 97/16190 | 5/1997 | WIPO . |

OTHER PUBLICATIONS

Dennis A. Holt, et al., "Structure Activity Studies of Synthetic FKBP Ligands as Peptidyl–Prolyl Isomerase Inhibitors", *Bioorganic and Medicinal Chemistry Letters*, vol. 4, No. 2, pp. 315–320, (1994).

Maginni, et al. 'Imino Diels–Alder Cycloadditions: An Application to the Synthesis of (+/–)–Aristeromycin', vol.31, No. 43, Tetrahedron Letters 1990.

*Primary Examiner*—Zinna Northington Davis
*Assistant Examiner*—Binta Robinson
*Attorney, Agent, or Firm*—Peter C. Richardson; Paul H. Ginsburg; E. Victor Donahue

[57] ABSTRACT

This invention relates to novel azabicyclic compounds of the formula

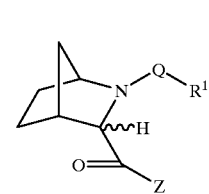

(I)

wherein $R^1$, Q and Z are defined as in the specification, pharmaceutical compositions containing them, and the use of such compounds for the treatment of neurodegenerative diseases and other disorders involving nerve damage.

19 Claims, No Drawings

AZABICYCLIC ROTOMASE INHIBITORS

The present application claims priority under 35 USC section 119 of U.S. Provisional Specification 60/079,138, filed Mar. 24, 1998.

This invention relates to novel azabicyclic compounds that inhibit the cis-trans prolyl isomerase (rotomase) activity of the FK-506-Binding Protein FKBP-12, pharmaceutical compositions containing such compounds and methods of using such compounds for the treatment of neurodegenerative diseases and other disorders involving nerve damage.

The chronic neurodegenerative conditions, Alzheimer's disease (AD) and Parkinson's disease (PD) result from the progressive death of different populations of neurons in the CNS. The behavioral manifestations of this neuron death do not become apparent until the pathological process is well underway and substantial neuron loss has already occurred. Thus, an agent that would halt the progressive loss of neurons and restore function through promoting regeneration of surviving neurons would be an effective therapy for these diseases. The brain produces neurotrophic factors which theoretically could produce these effects. However, since these factors are large proteins with poor bioavailability, it has not been possible to evaluate this therapeutic approach in man.

In 1994, it was reported that the immunosuppressant FK-506 promoted neurite outgrowth in vitro in neuronal cell line and culture models. (See Lyons et al., *Pro. Nat'l. Acad. Sci. U.S.A.*, 1994, 91, 3191–95; and Snyder et al., *Nature Medicine*, Vol. 1, No. 1, January, 1995, 32–37). Both Guilford Pharmaceuticals Inc. and Vertex Pharmaceuticals Inc. have developed structurally related compounds that retain potent neurotrophic activity but lack inhibitory action at the protein phosphatase calcineurin and, therefore, lack immunosuppressant activity. (See World Patent Application WO 96/40140, published Dec. 19, 1996; World Patent Application WO 96/40633, published Dec. 19, 1996; and World Patent Application WO 94/07858, published Apr. 14, 1994). All of the patent applications and literature articles referred to above are incorporated herein by reference in their entireties.

It is hypothesized that the neurotrophic effect of these compounds results from a high affinity interaction with the FK-506-Binding Protein, FKBP-12. As indicated in WO 96/40140 and WO 96/40633, referred to above, the neurotrophic activity of the Vertex and Guilford compounds correlates closely with the ability to to inhibit the rotamase activity of this protein. However, the mechanism by which this interaction with FKBP-12 results in a neurotrophic effect is at present unknown. Guilford has explored the scope of neurotrophic activity that can be realized through this neurotrophic/non-immunosuppressant class of compounds. They have found that these compounds can promote axon regeneration after facial nerve crush and sciatic nerve crush in rat. (See WO 96/40140 and WO 96/40633, referred to above). It was also observed in rat that these compounds promote the functional regeneration of dopamine neurons damaged with the toxin MPTP. This regenerative effect was observed if treatment was delayed as much as one month after the toxic insult.

The compounds of formula I, which are described below, are potent inhibitors of the rotomase activity of FKBP-12, but lack inhibitory action at the protein phosphatase calcineurin, and are useful as neurotropic agents in the treatment of neurodegenerative diseases such as Alzheimer's disease, amyotropic lateral sclerosis (ALS), Huntingon's disease and Parkinson's disease, without exhibiting immunosuppressant activity. Such compounds have been found to stimulate neurite outgrowth in chick dorsal root ganglia in the presence of nerve growth factor.

SUMMARY OF THE INVENTION

This invention relates to compounds of the formula I

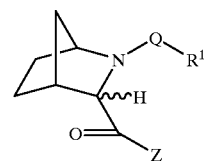

(I)

wherein Q is —S(=O)$_2$—, —C(=O)—N(H)—, —C(=O)—CH$_2$—, —CH$_2$C(=O)—, —C(=O)—C(=O)—, —C(=S)— —C(=O)— or C(=O)—CH(OH)—;

R$^1$ is phenyl, phenyl-(C$_1$–C$_3$)alkyl or (C$_1$–C$_6$)alkyl, and wherein the cyclic and (C$_1$–C$_6$)alkyl moieties of R$^1$ may optionally be substituted with from zero to three substituents that are selected, independently, from hydroxy, formate, acetate, (C$_1$–C$_4$)alkyl, nitro, cyano, halo and NR$^4$R$^5$ wherein R$^4$ and R$^5$ are selected, independently, from hydrogen and (C$_1$–C$_4$)alkyl;

Z is —XCHR$^2$R$^3$ or —CHR$^9$R$^{10}$;

X is oxygen or NR$^8$ wherein R$^8$ is hydrogen or (C$_1$–C$_6$) alkyl;

R$^2$ and R$^3$ are selected, independently, from hydrogen, (C$_1$–C$_{12}$) straight or branched alkyl, (C$_5$–C$_8$)cycloalkyl, (C$_5$–C$_8$)cycloalkyl-(C$_1$–C$_{12}$) straight or branched alkyl, aryl, aryl-(C$_1$–C$_{12}$)straight or branched alkyl, wherein said aryl is selected from phenyl, 1-naphthyl, and 2-naphthyl, heteroaryl and heteroaryl-(C$_1$–C$_{12}$) straight or branched alkyl, wherein said heteroaryl is selected from, 2-furyl, 3-furyl, 2-thienyl, 2-pyridyl, 3-pyridyl and 4-pyridyl, and wherein one or two of the CH$_2$ moieties of said phenyl-(C$_1$–C$_{12}$)alkyl, (C$_5$–C$_8$) cycloalkyl-(C$_1$–C$_{12}$) straight or branched alkyl or heteroaryl-(C$_1$–C$_{12}$) straight or branched alkyl may optionally and independently be replaced with NH or C=O, and wherein each of the cyclic and acyclic moieties of R$^2$ and R$^3$ may optionally be substituted with from zero to three substituents that are selected, independently, from halo, hydroxy, cyano, nitro, trifluoromethyl, NR$^6$R$^7$ wherein R$^6$ and R$^7$ are defined as R$^4$ and R$^5$ above, (C$_1$–C$_4$)alkyl, (C$_1$–C$_4$)alkoxy, phenoxy and benzyloxy;

or R$^2$ and R$^3$, together with the carbon to which they are attached, from a group of the formula

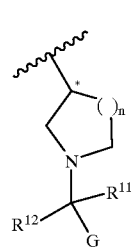

(A)

wherein n is one or two, R$^{11}$ and R$^{12}$ are selected, independently, from hydrogen, (C$_1$–C$_6$)alkyl and fluorine, or together form an oxo (=O) group, and G is selected form four to seven membered monocyclic, or ten to fourteen membered bicyclic carbocyclic rings that can be saturated or unsaturated, wherein from one to three of the nonfused carbon atoms of said monocyclic rings, and from one to five of the carbon atoms of said bicyclic rings that are not part of the benzo ring shown in formula I, may optionally and independently be replaced by nitrogen, oxygen or sulfur, and wherein said monocyclic and bicyclic rings may optionally be substituted with one or more substituents, preferably from zero to two substituents for the monocyclic rings and from zero to three substituents for the bicyclic rings, wherein said substituents are selected, independently, from ($C_1$–$C_6$) alkyl optionally substituted with from one to seven fluorine atoms, ($C_1$–$C_6$) alkoxy optionally substituted with from one to seven fluorine atoms, nitro, cyano, halo, amino, ($C_1$–$C_6$) alkylamino and [($C_1$–$C_6$) alkyl]$_2$amino; and $R^9$ and $R^{10}$ are defined as $R^2$ and $R^3$ are defined above;

with the proviso that $R^2$ and $R^3$ cannot both be hydrogen, and $R^9$ and $R^{10}$ cannot both be hydrogen;

and the pharmaceutically acceptable salts of such compounds.

Examples of preferred compounds of the formula I are those wherein the stereochemisty at the carbon atom of group "A" above that is marked with an asterisk is the S configuration, as depicted below:

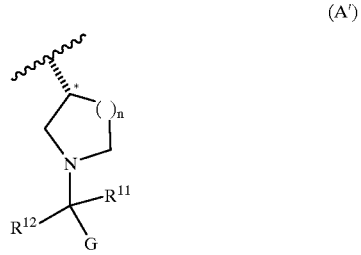

(A')

More specific embodiments of this invention relate to compounds of the formula I wherein none of the $R^1$, $R^2$ and $R^3$ groups are substituted.

Other more specific embodiments of this invention relate to compounds of the formula I wherein none of the alkyl moieties of the $R^1$, $R^2$, $R^3$, $R^9$ and $R^{10}$ groups are substituted.

Other more specific embodiments of this invention relate to compounds of the formula I wherein Z is —XCHR$^2$R$^3$ and X is oxygen.

Other more specific embodiments of this invention relate to compounds of the formula I wherein Z is —XCHR$^2$R$^3$ and X is NR$^8$.

Other more specific embodiments of this invention to compounds of the formula I wherein Z is —XCHR$^2$R$^3$ and Q is —S(=O)$_2$—.

Other more specific embodiments of this invention relate to compounds of the formula I wherein Z is —XCHR$^2$R$^3$ and Q is —C(=O)—CH$_2$—.

Other more specific embodiments of this invention relate to compounds of the formula I wherein Z is —XCHR$^2$R$^3$ and Q is —CH$_2$—C(=O)—.

Other more specific embodiments of this invention relate to compounds of the formula I wherein Z is —XCHR$^2$R$^3$ and Q is —C(=O)—C(=O)—.

Other more specific embodiments of this invention relate to compounds of the formula I wherein Z is —XCHR$^2$R$^3$ and Q is other than —C(=O)—C(=O)—.

Other more specific embodiments of this invention relate to compounds of the formula I wherein Z is —XCHR$^2$R$^3$ and Q is —C(=O)—CH(OH)—.

Other more specific embodiments of this invention relate to compounds of the formula I wherein Z is —XCHR$^2$R$^3$ and Q is —C(=O)—N(H)—.

Other more specific embodiments of this invention relate to compounds of the formula I wherein Z is —XCHR$^2$R$^3$ and Q is —C(=S)—C(=O)—.

Other more specific embodiments of this invention to compounds of the formula I wherein Z is —CHR$^9$R$^{10}$ and Q is —S(=O)$_2$—.

Other more specific embodiments of this invention relate to compounds of the formula I wherein Z is —CHR$^9$R$^{10}$ and Q is —C(=O)—CH$_2$—.

Other more specific embodiments of this invention relate to compounds of the formula I wherein Z is —CHR$^9$R$^{10}$ and Q is —CH$_2$—C(=O)—.

Other more specific embodiments of this invention relate to compounds of the formula I wherein Z is —CHR$^9$R$^{10}$ and Q is —C(=O)—C(=O)—.

Other more specific embodiments of this invention relate to compounds of the formula I wherein $R^2$ and $R^3$ do not, together with the carbon to which they are attached, form a ring.

Other more specific embodiments of this invention relate to compounds of the formula I wherein Z is —CHR$^9$R$^{10}$ and Q is other than —C(=O)—C(=O)—.

Other more specific embodiments of this invention relate to compounds of the formula I wherein Z is —CHR$^9$R$^{10}$ and Q is —C(=O)—CH(OH)—.

Other more specific embodiments of this invention relate to compounds of the formula I wherein Z is —CHR$^9$R$^{10}$ and Q is —C(=O)—N(H)—.

Other more specific embodiments of this invention relate to compounds of the formula I wherein Z is —CHR$^9$R$^{10}$ and Q is —C(=S)—C(=O)—.

Other more specific embodiments of this invention relate to compounds of the formula I wherein Z is —CHR$^2$R$^3$ and one of $R^2$ and $R^3$ is hydrogen and the other is selected from ($C_1$–$C_{12}$) straight or branched alkyl, ($C_5$–$C_8$)cycloalkyl, ($C_5$–$C_8$)cycloalkyl-($C_1$–$C_{12}$) straight or branched alkyl, phenyl and phenyl-($C_1$–$C_{12}$)straight or branched alkyl.

Other more specific embodiments of this invention relate to compounds of the formula I wherein Z is —CHR$^9$R$^{10}$ and one of $R^9$ and $R^{10}$ is hydrogen and the other is selected from ($C_1$–$C_{12}$) straight or branched alkyl, ($C_5$–$C_8$)cycloalkyl, ($C_5$–$C_8$)cycloalkyl-($C_1$–$C_{12}$) straight or branched alkyl, phenyl and phenyl-($C_1$–$C_{12}$)straight or branched alkyl.

Other more specific embodiments of this invention relate to compounds of the formula I wherein Z is —CHR$^9$R$^{10}$.

Examples of compounds of the formula I include the following:

1-(2-Cyclohexylmethanesulfonyl-2-aza-bicyclo[2.2.1] hept-3-yl)-5-quinolin-4-yl-pentan-1-one;

1-(2-Cyclohexylmethanesulfonyl-2-aza-bicyclo[2.2.1] hept-3-yl)-5-(1H-indazol-5-yl)-pentan-1-one;

1-(2-Cyclohexylmethanesulfonyl-2-aza-bicyclo[2.2.1] hept-3-yl)-5-(1H-indazol-6-yl)-pentan-1-one;

1-(2-Cyclohexylmethanesulfonyl-2-aza-bicyclo[2.2.1] hept-3-yl)-5-pyridin-2-yl-pentan-1-one;

1-(2-Phenylmethanesulfonyl-2-aza-bicyclo[2.2.1]hept-3-yl)-5-(3,4,5-trimethoxy-phenyl)-pentan-1-one; and 1-(2-Cyclohexylmethanesulfonyl-2-aza-bicyclo[2.2.1] hept-3-yl)-5-(3,4,5-trimethoxy-phenyl)-pentan-1-one.

This invention also relates to a pharmaceutical composition for the treatment of a disorder selected from neurodegenerative diseases and other disorders involving nerve damage such as Alzheimer's disease, amyotropic lateral sclerosis (ALS), Parkinson's disease, Huntington's disease, senile dementia of the Alzheimer's type, AIDS related neuropathies, brain damage associated with stroke or head trauma, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g., spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of auto-immune related disease resulting in damage to the central or peripheral nervous system (e.g. multiple sclerosis, myasthenia gravis, Guillain-Barré syndrome), dapsone ticks, bulbar and retrobulbar affections of the optic nerve (e.g., retinopathies and retrobulbar neuritis), prion diseases and hearing disorders (e.g., hearing loss due to neuron death, and tinnitus) in a mammal, including a human, comprising an amount of a compound of the formula I, or a pharmaceutically acceptable salt thereof, that is effective in the treatment of such disorder, and a pharmaceutically acceptable carrier.

This invention also relates to a method for the treatment of a disorder selected from neurodegenerative diseases and other disorders involving nerve damage such as Alzheimer's disease, Parkinson's disease, ALS, Huntington's disease, senile dementia of the Alzheimer's type, diabetic neuropathy, AIDS related neuropathies, brain damage associated with stroke or head trauma, all forms of degenerative disease affecting the central or peripheral nervous system (e.g. cerebellar-brainstem atrophies, syndromes of progressive ataxias), all forms of muscular dystrophy, progressive muscular atrophies, progressive bulbar muscular atrophy, physical or traumatic damage to the central or peripheral nervous system (e.g., spinal cord), herniated, ruptured or prolapsed intervertebrae disc syndromes, cervical spondylosis, plexus disorders, thoracic outlet syndromes, all forms of peripheral neuropathy (both diabetic and non-diabetic), trigeminal neuralgia, glossopharyngeal neuralgia, Bell's Palsy, all forms of auto-immune related disease resulting in damage of the central or peripheral nervous system (e.g. multiple sclerosis, myasthenia gravis, Guillain-Barré syndrome), dapsone ticks, bulbar and retrobulbar affections of the optic nerve (e.g., retinopathies and retrobulbar neuritis), prion diseases and hearing disorders (e.g., hearing loss due to neuron death, and tinnitus) in a mammal, including a human, comprising administering to a subject in need of said treatment an amount of a compound of the formula I, or a pharmaceutically acceptable salt thereof, that is effective in treating such disorder.

This invention also relates to a pharmaceutical composition for the treatment of a disorder the treatment of which can be effected or facilitated by inhibiting the rotomase activity of FKBP-12 in a mammal, including a human, comprising an amount of a compound of the formula I, or a pharmaceutically acceptable salt thereof, that is effective in the treatment of such disorder, and a pharmaceutically acceptable carrier.

This invention also relates to a method for the treatment of a disorder the treatment of which can be effected or facilitated by inhibiting the rotomase activity of FKBP-12 in a mammal, including a human, comprising administering to a subject in need of said treatment an amount of a compound of the formula I, or a pharmaceutically acceptable salt thereof, that is effective in treating such disorder.

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Unless otherwise indicated, "halo" and "halogen", as used herein, refer to fluorine, bromine, chlorine or iodine.

This invention includes all optical isomers and other stereoisomers of compounds of the formula I. When such compounds contain one or more chiral centers, it is understood that the invention includes racemic mixtures as well as all individual enantiomers, diastereomers and other stereoisomers of such compounds, as well as mixtures thereof. For example, this invention includes compounds wherein the substituent on the ring carbon atom that is adjacent to the ring nitrogen atom depicted in formula I is in the endo configuration, as well as the analogous compounds having the exo configuration and mixtures of compounds having both configurations.

The compounds of this invention include compounds identical to those described above but for the fact that one or more atoms are replaced by isotopes thereof (e.g., tritium or carbon-14 isotopes). Such compounds are useful as research and diagnostic tools in metabolism pharmokinetic studies and in binding assays.

This invention also includes the pharmaceutically acceptable acid and base addition salts of compounds of the formula I.

The term "alkyl", as used herein, unless otherwise indicated, includes saturated monovalent hydrocarbon radicals having straight branched or cyclic moieties or combinations thereof.

The term "alkoxy", as used herein, unless otherwise indicated, means —O-alkyl, where "alkyl" is defined as above.

DETAILED DESCRIPTION OF THE INVENTION

Compounds of the formula I and their pharmaceutically acceptable salts can be prepared as described below. In the reaction schemes and discussion that follow, formula I and groups Q, X, $R^1$, $R^2$, $R^3$, $R^4$, $R^5$, $R^6$, $R^7$, $R^8$, $R^9$, and $R^{10}$ are defined as above and Et=ethyl.

SCHEME 1
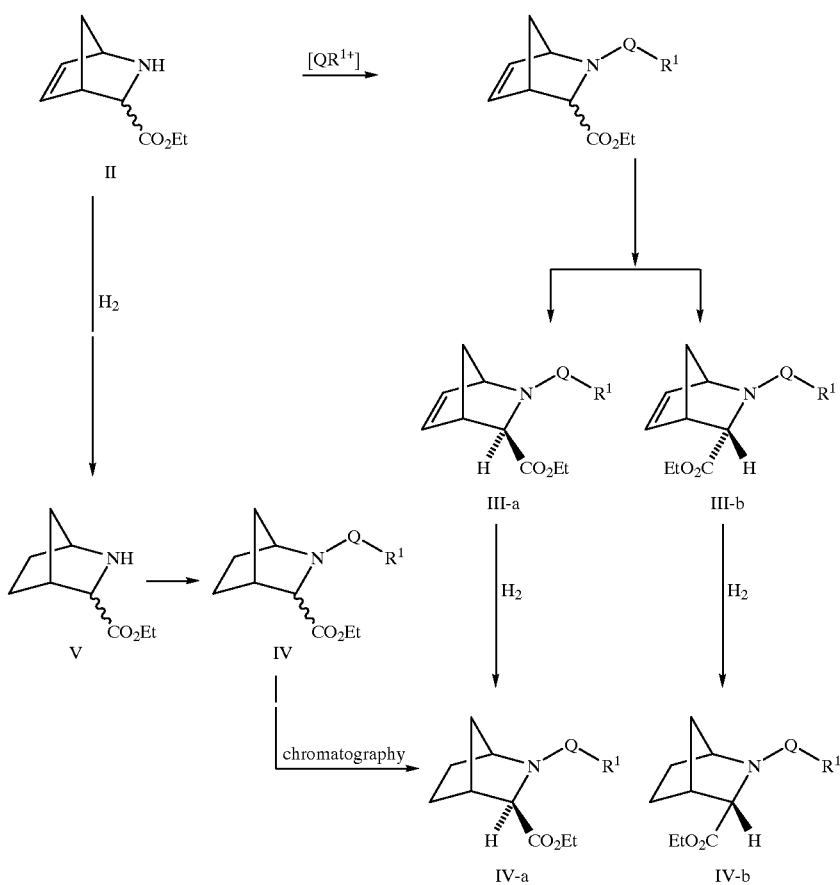
SCHEME 2
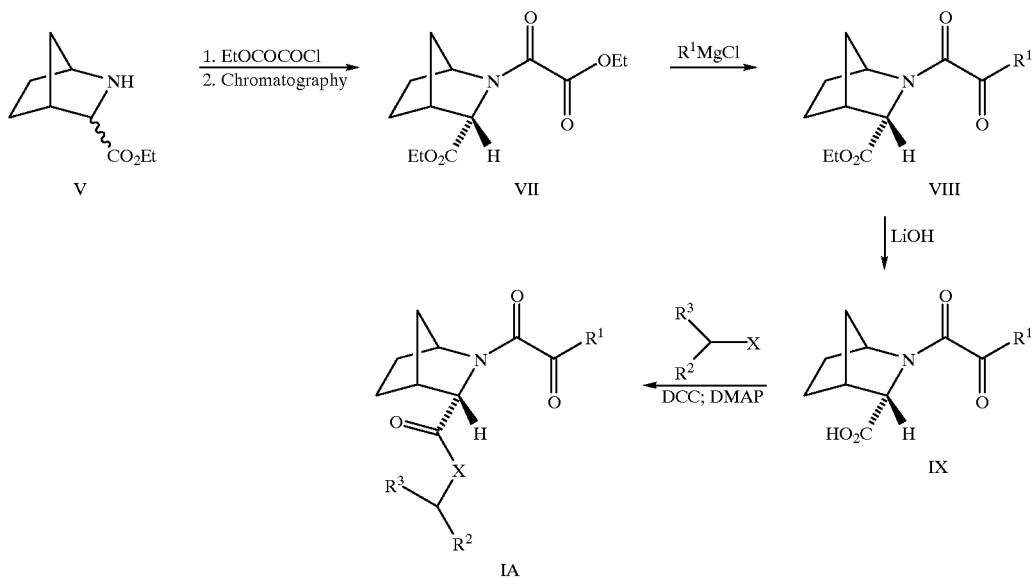

SCHEME 3
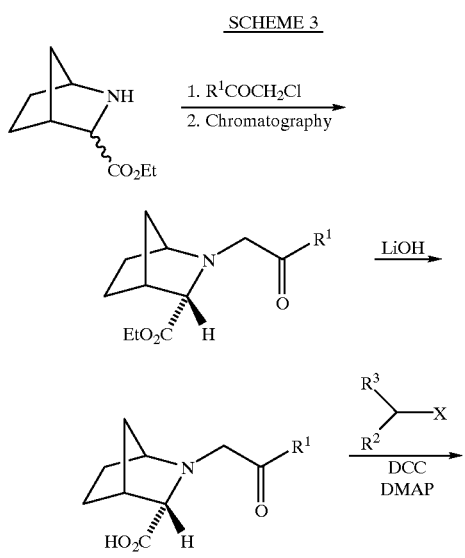
SCHEME 4
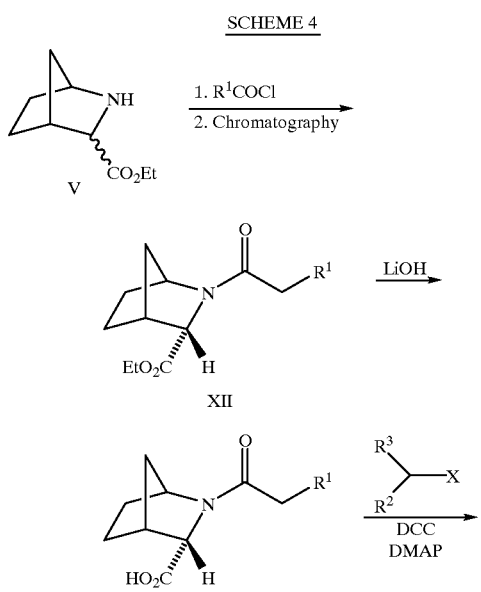
SCHEME 5
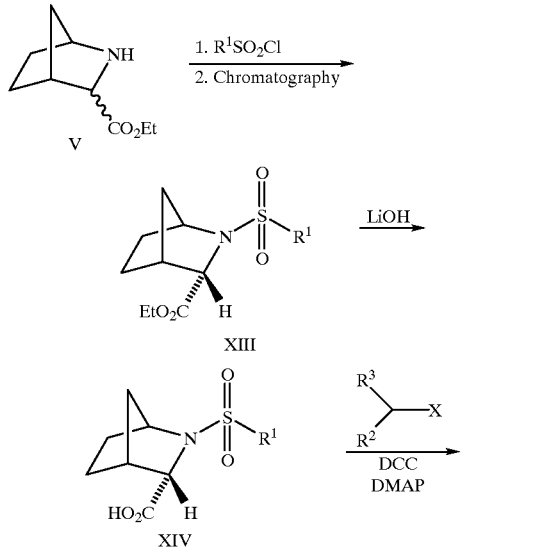
SCHEME 6
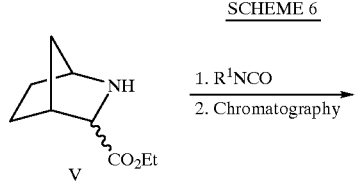

-continued
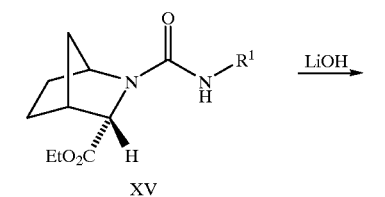
XV
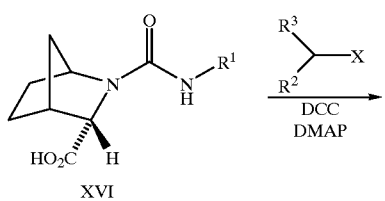
XVI
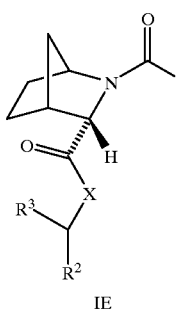
IE
SCHEME 7
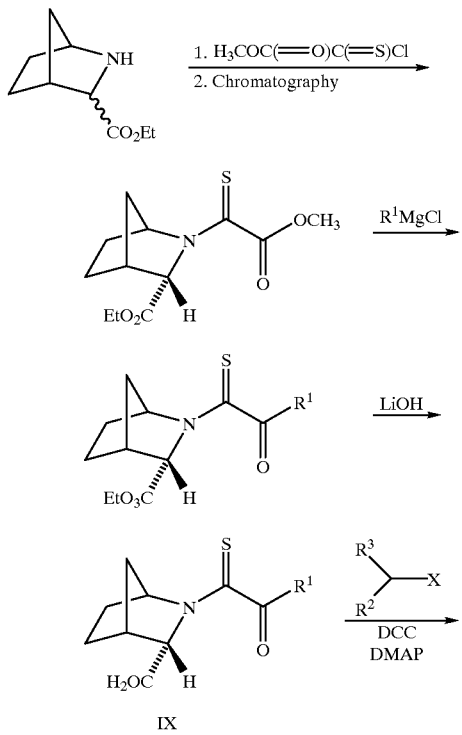
IX
-continued
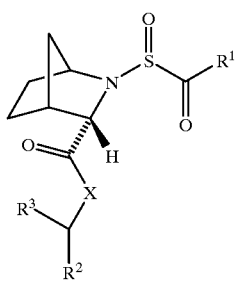
SCHEME 8
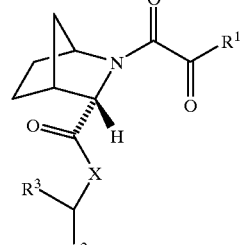
IA
↓ NaBH$_4$
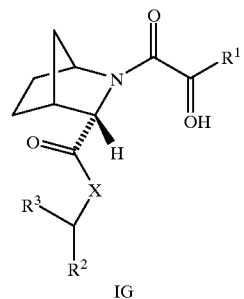
IG
Scheme 9
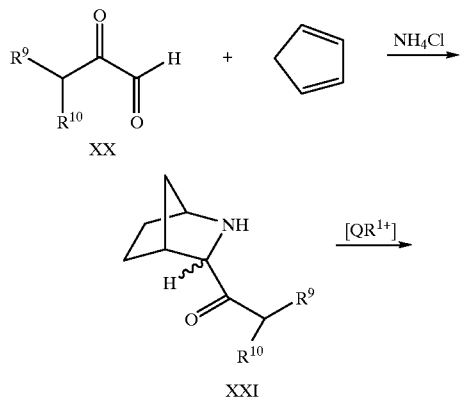
XXI -continued

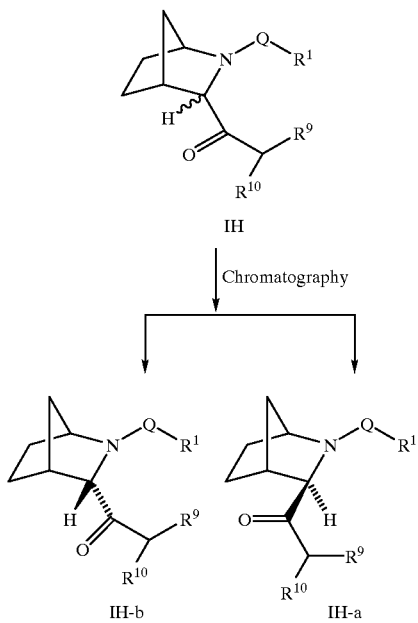

Scheme 1 illustrates a method for separating the exo and endo isomers of chemical intermediates that are used in the synthesis of compounds of the formula I. Scheme 1 illustrates, specifically, alternative sequences of the reactions that involve hydrogenation, addition of the $QR^1$ sidechain and the chromatographic separation of the endo and exo isomers. The particular reactions that are used to add specific $QR^1$ sidechains to the ring nitrogen are illustrated in the subsequent schemes and described below for different Q groups. The chromatographic separation step is described in Example 1. As illustrated in Scheme 1, the hydrogenation of the double bond in the azabicyclo[2.2.1]heptene ring may be carried out before or after addition of the $QR^1$ sidechain and the chromatographic separation of the exo and endo isomers. Such hydrogenation is carried out under standard conditions that are well known to those of skill in the art.

The structures in Schemes 2 through 8 have been drawn to depict the syntheses of the endo isomers of various compounds of the formula I. The syntheses described, however, can also be used to prepare the corresponding exo isomers by isolating the appropriate exo intermediates in the chromatography steps of the Schemes 2 through 7, and then subjecting such intermediates to the remaining reaction sequences in such schemes. The product of formula I that is produced by the procedure of Scheme 8 will have the exo configuration if the reactant illustrated in that scheme has the exo configuration.

Scheme 2 illustrates the preparation of compounds of the formula I wherein Q is —C(=O)—C(=O)—, which are also referred to as compounds of the formula IA, from compounds of the formula V. Referring to Scheme 2, the compound of formula V can be prepared by hydrogenating, under standard conditions well known to those of skill in the art, a mixture of exo- and endo-2-aza-bicyclo[2.2.1]hept-5-ene-3-carboxylic acid ethyl esters, which can be prepared using the procedure described by Hurst House et al., *J. Chem. Soc. Perkin Trans. I*, 1995, (2419, 2425) and Greico et al., *J. Am. Chem. Soc.*, 1985, 107, (1768–1774). The compound of formula V is then reacted with a compound of the formula $R^{11}QOJ$, wherein J is benzyl or $(C_1-C_3)$alkyl, Q is —C(=C)—C(=O)— or —C(=O)—C(=S)— and $R^{11}$ is chloro, bromo or hydroxy. Preferably, $R^{11}QOJ$ is ethyl oxalyl chloride when Q is —C(=O)—C(=O)— and $R^{11}QOJ$ is $H_3COC(=O)-C(=S)Cl$ when Q is —C(=O)—C(=S)—. This reaction is typically carried out in a solvent such a methylene chloride or dichloroethane, preferably in a mixture of methylene chloride and triethylamine (TEA), at a temperature from about 0° C. to about the reflux temperature of the solvent, preferably at about room temperature, to form a mixture of endo and exo isomers of the compound of formula VII. (Structural formula VII, as drawn, refers to the endo isomer). The endo and exo isomers can then be chromatographically separated as described in Example 1. After separation, the endo (or exo) isomer is reacted with a compound of the formula $R^1MgCl$, $R^1MgBr$ or $R^1MgI$, preferably $R^1MgCl$, in an appropriate solvent such as ether or tetrahydrofuran (THF), at a temperature from about −78° C. to about 0° C., preferably at about −78° C. The resulting compound of formula VII can then be converted into the corresponding carboxcyclic acid of formula IX by reacting it with aqueous lithium hydroxide. This reaction is preferably carried out in a lower alcohol solvent, preferably methanol, at a temperature from about 0° C. to about the reflux temperature, of the reaction mixture, preferably at about room temperature.

The desired compound of the formula IA can then be formed as follows. The carboxylic acid of formula IX is reacted with the compound of the formula $XCH(R^2)(R^3)$ in the presence of dicyclohexylcarbodiimide (DCC) and 4-dimethylaminopyridine (DMP). Suitable solvents for this reaction include lower alcohols, pyridine, THF, ethyl acetate, methylene chloride and chloroform. The reaction temperature may range from about 0° C. to about the reflux temperature of the reaction mixture. Preferably, the reaction is carried out at about room temperature.

To form compounds of the formula IA wherein $R^2$ and $R^3$, together with the carbon to which they are attached, form a ring, it is preferable to react the carboxylic acid of formula IX with the compound of formula $XCH(R^2)(R^3)$ in the presence of a tertiary amine base such as triethylamine, in a nonprotic solvent, at a temperature from about 0° C. to about 60° C., preferably at about room temperature. Suitable solvents include ethyl acetate, dioxane and methylene chloride.

Schemes 3–7 illustrate methods of synthesizing compounds of formula I wherein Q is, respectively, —CH$_2$—C(=O)—, —C(=O)—CH$_2$—, —S(=O)$_2$—, —C(=O)—N(H)—, and —C(=S)—C(=O)—. The procedures set forth in these schemes differ from those of Scheme 2 only in the addition of $QR^1$ sidechain. Scheme 8 illustrates the preparation of compounds of the formula I wherein Q is —C(=O)—CH(OH)— by reduction of the corresponding compounds wherein Q is —C(=O)—C(=O)—.

As shown in Scheme 3, when Q is —CH$_2$—C(=O)—, the $QR^1$ sidechain is added to the ring nitrogen of structure V by reacting the compound of formula V with a compound of the formula $R^1COCH_2W$ wherein W is chloro, bromo, iodo, triflate, mesylate or tosylate, preferably chloro or bromo. This reaction is preferably conducted in the presence of a catalytic amount of potassium iodide (from about 0.1 to about 1.0 equivalent), at a temperature from about room temperature to about the reflux temperature. Suitable solvents include acetone, N, N-dimethylformamide, THF, acetone and pyridine. Preferably, the reaction is conducted in an acetone solvent and allowed to reflux for about 2–8 hours. In this reaction, one equivalent of acid (e.g., hydrochloric acid or hydroiodic acid) is formed. Therefore, an external base (e.g, sodium carbonate, triethylamine (TEA) or sodium bicarbonate) is preferably added to react with it.

The addition of the QR$^1$ sidechain may be accomplished as follows when Q is —C(=O)—CH$_2$—. As shown in Scheme 4, the compound of formula V is reacted with a compound of the formula R$^1$COW wherein W is chloro, bromo or hydroxy. The pH of the reaction mixture is generally about 8 to about 9 and the reaction temperature can range from about room temperature to about the reflux temperature of the reaction mixture. Preferably, the reaction is conducted at about reflux temperature. This reaction is generally concucted in a solvent such as water/acetone, methylene chloride, THF, TEA, or chloroform. The preferred solvent is water/acetone. This reaction, like the analogous reaction in Scheme 3, produces 1 equivalent of acid. Preferably, an equivalent amount of an external base, such as those described above, is added to react with it.

When Q is —S(=O)$_2$—, the QR$^1$ sidechain can be added, as shown in Scheme 5, by reacting the compound of formula V with a compound of the formula R$^1$SO$_2$Cl, or R$^1$SO$_2$Br, using similar solvents and conditions as those described above for the addition of the QR$^1$ sidechain when Q is —C(=O)—CH$_2$—. This reaction is preferably allowed to react for about 2–12 hours.

Refering to Scheme 6, the QR$^1$ sidechain, when Q is —C(=O)—N(H)—, is added by reacting the compound of formula V with a compound of the formula R$^1$NCO for about 2–12 hours at a temperature from about 0° C. to about the reflux temperature of the mixture, preferably at about the reflux temperature, in a solvent such as THF, ethyl acetate or methylene chloride.

Referring to Scheme 7, when Q is —C(=S)—C(=O)—, the QR$^1$ sidechain can be added in a manner analogous to that described above for the formation of compounds of the formulas VII and VIII in Scheme 2, but replacing Q=—C(=O)—C(=O)— with Q=—C(=S)—C(=O)—. Preferably, the compound of formula V is reacted with the compound H$_3$COC(=O)C(=S)Cl, using conditions similar to those described in Example 1, separating the endo and exo isomers as described in Example 1, and then reacting the exo isomer of formula XVII with a compound of the formula R$^1$MgW, wherein W is chloro, bromo or iodo, using standard Grignard conditions. Preferably, the solvent used for the reaction with H$_3$COC(=O)C(=S)Cl (or with a similar compound as described above for Scheme 2) is a mixture of methylene chloride and TEA. Other nonprotic solvents such as THF, chloroform and ethyl acetate can also be used. A base such as TEA, sodium carbonate or sodium bicarbonate is preferably added to the reaction mixture to react with the hydrochloric acid that is formed during the reaction.

The reduction of compounds of formula IA to form the analogous compounds of formula IG, depicted in Scheme 8, can be carried out using any of a variety of methods that are well known to those of skill in the art. For example, the reduction can be carried out using sodium borohydride as the reducing agent and a lower alcohol solvent (preferably methanol) and allowing the reaction mixture to react at a temperature from about room temperature to about the reflux temperature, preferable at about the reflux temperature.

Scheme 9 illustrates a method of preparing compounds of the formula I wherein Z is —CHR$^9$R$^{10}$. Referring to Scheme 9, the appropriate compound of formula XX is reacted with cyclopentadiene and an ammonium source (e.g., ammonia, an ammonium halide or benzylamine, etc.), at a temperature from about 0° C. to about 60° C., preferably in aqueous ammonium chloride at about room temperature, to form the corresponding compound of formula XXI. Appropriate solvents include protic and aprotic solvents such as water and benzene. This reaction proceeds via an imine intermediate of the formula

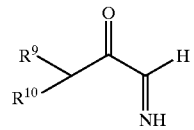

and is preferably carried out in the presence of a catalytic amount of acid when the ammonia source is other than an ammonium salt. The compound of formula XXI is then converted into the corresponding compound of formula IH using the procedure depicted in Scheme 1 and described above for forming compounds of the formula III from those of formula II. The endo and exo isomers of formula IH-b and IH-a, respectively, can be separated by chromatography, as described in Example 1.

The starting materials used in the procedures described above are either commercially available or can be readily made by those of skill in the art.

The compounds of the formula I that are basic in nature are capable of forming a wide variety of different salts with various inorganic and organic acids. The acids that are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1-methylene-bis-(2-hydroxy-3-naphthoate)] salts. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of the formula I that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases that are used as reagents to prepare the pharmaceutically acceptable base salts of this invention are those which form non-toxic base salts with the acidic compounds of formulae I, II and III. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product of yields of the desired final product.

The compounds of the formula I and the pharmaceutically acceptable salts thereof can be administered via either the oral, parenteral or topical routes. In general, these compounds are most desirably administered in dosages ranging from about 1.0 mg to about 1000 mg per day, preferably from about 25 mg to about 300 mg per day, in single or divided doses (e.g, from one to four doses per day), although variations will necessarily occur depending upon the weight and condition of the subject being treated and the particular route of administration chosen. Variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The activity of the compounds of the present invention as inhibitors of the rotomase activity of FKBP-12 can be determined using the assays described by Kofron et al., *Biochemistry,* 30, 6127, 1991, Takahashi et al., *Nature,* 337, 473, 1989, and Fisher et al., *Biochem. and Biophys. Acta,* 791 87, 1984. The present inventors used the assay described below, which is a slightly modified version of the foregoing assays.

Materials

Assay Buffer:

10 mM Tris (Sigma, #T 1503)

1 mM EDTA (Sigma, #M6250)

pH adjusted to 7.6

Substrate

L-succinyl-ala-leu-pro-phe-AMC (from Bachem, specially ordered)

dissolved in dry TFE (trifluoroethanol) with 470 mM LiCl

Enzymes

1) Human Recombinant FK-Binding Protein (FKBP-12), purified from *E. coli* from Sigma, #F-5398, 1,7 mg protein/ml solution in 10 mM

HEPES

2) Alpha-chymotrypsin (sigma #C-4129) 10 mg/ml solution

Assay Procedure

The assay is performed using a PTI fluorescence instrument (Photon Technology International), with an attaching cooling circulator. Test compounds and FKBP-12 (final concentration, 500 nM) are placed in a 1 cm plastic cuvette and incubated at room temperature for one half hour. The curvette is then placed on ice for an addition 15 minutes and alpha-chymotrypsin (100 microliters of a 10 mg/ml solution) is added. The cuvette is placed in the PTI and cooled for an additional 15 minutes at 0.0° C. The reaction is started by injecting the substrate (final concentration 0.5 micromolar) into the curvette. The excitation wavelength is 370 nm and the emission wavelength is 470 nm. Recording of the emission fluorescence continues for 300 seconds.

Data Analysis

The percent inhibition of each compound is calculated by:

% inh=100 * (1−(kobs-kbkg)/(kctrl-kbkg))

where kobs=rate of assay with test compound kctrl=rate of assay with FKBP and no drug kbkg=rate of assay with no FKBP or test compound When tested in accordance with the above procedure, the compounds of the formula I, the synthesis of which is illustrated in the experimental examples that follow, were found to exhibit 50% inhibition at concentrations less than 1.5 micromolar.

Preparation of Chick Dorsal Root Ganglia (DRG) Cultures

Dorsal root ganglia are isolated and cultured from embryonic day 9 chicks according to the procedure of Nishi (Methods in Cell Biology 1996, Vol. 51, pp. 249–263). Eggs are sterilised by squirting the entire surface with 70% ethanol. The egg is cracked and contents emptied into a 100 mm or larger petri dish. The embryo is isolated and transferred to a dish containing Ca2+/Mg2+-free Tyrode's buffer. The head, limbs, anterior abdomen and thorax are cut away, and the strip of body wall containing the spinal column is isolated. This strip is transferred to another dish containing the same buffer and cleaned of remaining organs and blood vessels to expose the spinal column. While using one pair of Dumont No. 5 forceps to anchor the spinal column, another pair is used with a pinching action to cut away the column, exposing the spinal cord and attached DRGS. The individual ganglia are easily seen between the segments of the spinal column, and can then be "plucked" away using Dumont No. 5 forceps. Any remaining nerve roots are removed. The ganglia are transferred to a 35 mm dish containing buffer and kept on ice until a number of ganglia are collected. Individual ganglia are then transferred directly into collagen-coated 24 well culture plates containing Neurobasal medium+B27 supplements. After allowing 4 hours for the ganglia to adhere, test compounds are added. Neurite outgrowth is assessed after an additional 24–48 hours. For each treatment group, at least 4 to 6 ganglia are examined, and scored by estimating the extent of neurite outgrowth relative to the diameter of the ganglion.

Quantification of Chick DRG Neurite Outgrowth

Dorsal root ganglia were cultured for 48 hours, fixed in formalin and stained with Coomassie blue. Initially, the explant treatments were evaluated by using neurite length. The explant was divided into 4 quadrants, the longest neurite in each quadrant measured with a stage micrometer and the average of those measurements used as the measurement for that explant. This method proved time consuming, did not take into consideration density differences that were obvious visually, and consequently was not sensitive enough to pick up significant differences from control in any dose of NGF (nerve growth factor) lower than 10 ng/ml.

A image analysis system with MCID software is used to measure the relative optical density. Using the digitized image of each ganglia, 4 circular samples are taken (diameter=260 microns) immediately adjacent to the explant and 4 more samples immediately adjacent to the first. The resulting number reflects the average ROD with the sample area. Inner and outer averages minus background are reported.

Two separate measurements (inner and outer) were made because of the much larger halo of outgrowth seen with NGF treatment. It was not readily apparent which might be the more useful sample area.

The present invention is illustrated by the following examples. It will be understood, however, that the invention is not limited to the specific details of these examples.

EXAMPLE 1

2-Ethoxyoxalyl-2-aza-bicyclo[2.2.1]hept-5-ene-endo-3-carboxylic acid ethyl ester and 2-Ethoxyoxalyl-2-Ethoxyoxalyl-2-aza-bicyclo[2.2.1]hept-5-ene-exo-3-carboxylic acid ethyl ester A mixture of exo- and endo-2-aza-bicyclo[2.2.1]hept-5-ene-3-carboxylic acid ethyl esters were prepared using the procedure outlined by Hursthouse and co-workers (*J. Chem. Soc. Perkin Trans. I*, 1995, 2419–2425) and Greico and co-workers (*J. Am. Chem. Soc.* 1985, 107, 1768–1774). To 1.67 g (10.0 mmol) of the above mixture dissolved in 10 ml of methylene chloride was added 1.11 mL (10.0 mmol) of ethyl oxalyl chloride and 1.66 mL (11.9 mmol) of triethylamine. The mixture was stirred at room temperature for 25 hours. The solvent was evaporated and the residue redissolved in ethyl acetate. The ethyl acetate solution was washed with saturated sodium bicarbonate, dried with anhydrous sodium sulfate and evaporated to yield 2.8 grams of a yellow gum. This material was chromatographed on 50 grams of silica using a 1:3 mixture of ethyl acetate and hexanes as the elutant. Appropriate fractions were combined to first yield 400 mg of 2-ethoxyoxalyl-2-aza-bicyclo[2.2.1]hept-5-ene-exo-carboxylic acid ethyl ester (clear oil) followed by 1.80 grams of 2-ethoxyoxalyl-2-aza-bicyclo[2.2.1] hept-5-ene-endo3-carboxylic acid ethyl ester (oil). Spectral data indicate that 2-ethoxyoxalyl-2-aza-bicyclo[2.2.1]hept-5-ene-endo-e-carboxylic acid ethyl ester exists as a 3:1 mixture of rotamers: $^1$H NMR (CDCl$_3$)δ6.30 (m, 1 H),5.9–6.10(m, 1 H), 4.9–5.1 (m, 1 H), 4.75, 4.25 (m, 1 H), 3.85–4.18 (m, 4 H), 3.32–3.5 (m, 1 H) 1.47–1.65 (m, 2 H), 1.0–1.2 (m, 6 H). $^{13}$C NMR (CDCl$_3$, ppm) major rotamer peaks: 169.9, 161.5, 157.7, 136.4, 134.7, 61.4, 61.2, 60.8, 59.6, 48.5, 48.1, 13.9, 13.6. Mass spectrum:m/e=268(p+1). RF(1:1 hexanes:ethyl acetane)=0.5. Spectral data indicate that 2-ethoxyoxalyl-2-aza-bicyclo[2.2.1]hept-5-ene-exo-3-carboxylic acid ethyl ester exists as a 1:1 mixture of rotamers: $^1$H NMR (CDCl$_3$) δ 6.35 (s, 1 H), 6.32 (s, 1 H), 5.0, 5.2 (s, 1 H), 4.0–4.45 (m, 4 H), 4.0, 3.6 (s,1 H), 3.25, 3.35 (s, 1 H), 1.7, 2.0 (d, 1 H), 1.4, 1.5 (d, 1 H), 1.1–1.3 (m, 6 H). Mass spectrum: m.e=268 (p+1). Rf (1:1 hexanes:ethyl acetate)=0.6.

EXAMPLE 2

2-Ethoxyoxalyl-2-aza-bicyclo[2.2.1]heptane-3-endo-carboxylic acid ethyl ester

A solution of 1.8 grams of 2-ethoxyoxalyl-2-aza-bicyclo[2.2.1]hept-5-ene-endo3-carboxylic acid ethyl ester dissolved in 50 mL of methanol was hydrogenated at 50 psi for 14 hours in the presence of 200 mg of 10% Pd/C. The reaction mixture was filtered and the solvent evaporated to yield 1.55 g of 2-ethoxyoxalyl-2-aza-bicyclo[2.2.1]heptane-3-endo-carboxylic acid ethyl ester as a yellow gum.

Spectral data indicate that 2-ethoxyoxalyl-2-aza-bicyclo[2.2.1]heptane-3-endo-carboxylic acid ethyl ester exists as an approximate 1:1 ratio of rotomers: $^1$H NMR (CDCl$_3$) δ 4.75, 4.60 (s, 1 H), 4.55, 4.25 (s, 1 H), 4.05–4.3 (m, 4 H), 2.8 (m, 1 H), 1.6–1.8 (m, 3 H), 1.1–1.4 (m, 6 H). Mass spectrum: m/e=270 (p+1). Rf (1:1 hexanes:ethyl acetate)= 0.58.

EXAMPLE 3

Ethoxyoxalyl-2-aza-bicyclo[2.2.1]heptane-3-exo-carboxylic acid ethyl ester $^1$H NMR (CDCl$_3$) δ 4.55, 4.45 (s, 1 H), 4.32, 3.86 (s, 1 H), 4.18 (m, 1 H), 3.95–4.25 (m, 4 H), 2.72, 2.6 (s, 1 H), 1.0–2.0 (m, 10 H). Mass spectrum: m/e=270 (p+1). Rf (1:1 hexanes:ethyl acetate)=0.68.

EXAMPLE 4

2-(3,3-Dimethyl-2-oxo-pentanoy)-2-aza-bicyclo[2.2.1]heptane-3-endo-carboxylic acid ethyl ester A solution of 1.10 grams (4.09 mmol) of 2-ethoxyoxalyl-2-aza-bicyclo[2.2.1]heptane-3-endo-carboxylic acid ethyl ester dissolved in 20 mL of ether was cooled to −78° C. under a nitrogen atmosphere. To this solution was added dropwise 5.45 mL (5.45 mmol) of a 1 molar solution of 1,1-dimethylpropylmagnesium chloride in ether. The reaction was stirred at −78° C. for 3 hours. After 3 hours, the cold reaction mixture was quenched with saturated ammonium chloride. The mixture was warmed to room temperature and extracted with ethyl acetate. The ethyl acetate extracts were dried and evaporated. The residue was chromatographed on silica using hexanes containing 12% ethyl acetate as the elutant. Appropriate fractions were combined and evaporated to yield 600 mg Of 2-(3,3-dimethyl-2-oxo-pentanoyl)-2-aza-bicyclo[2.2.1]heptane-3-endo-carboxylic acid ethyl ester as an oil. Rf (1:1 hexanes:ethyl acetate) 0.80. The $^1$H NMR is a mixture of rotomers: $^1$H NMR (CDCl$_3$) δ 3.8–4.6 (m, 4 H), 2.7 (m, 1 H), 1.25–1.7 (m, 8 H), 0.6–1.2 (m, 12 H). Mass spectrum: m/e=296 (p+1)

EXAMPLE 5
2-(3,3-Dimethyl-2-oxo-pentanoyl)-2-aza-bicyclo[2.2.1] heptane-3-exo-carboxylic acid ethyl ester Rf (1:1 hexanes:ethyl acetate)=0.80. Spectral data indicate this compound is a mixture of rotomers. Principal $^{13}$C NMR peaks (CDCl$_3$, ppm) 204, 169.1, 163.5, 63.3, 61.1, 58.6, 46.8, 41.0, 35.3, 32.1, 31.8, 27.3, 24.1, 23.0, 14.0, 8.8. $^1$H NMR (CDCl$_3$) δ 3.8–4.6 (m, 4 H), 2.7 (m, 1 H), 1.25–1.7 (m, 8 H), 0.6–1.2 (m, 12 H). Mass spectrum: m/e=296 (p+1).

EXAMPLE 6
2-(3,3-Dimethyl-2-oxo-pentanoyl)-2-aza-bicyclo[2.2.1] heptane-3-endo-carboxylic acid A mixture of 600 mg (2.03 mmol) 2-(3,3-dimethyl-2-oxo-pentanoyl)-2-aza bicyclo[2.2.1]heptane-3-endo-carboxylic acid ethyl ester and 2.8 mL mmol) of 1N aqueous lithium hydroxide in 18 mL of methanol was stirred at room temperature for 4 days. The solvent was evaporated and the residue was partitioned between ethyl acetate and water, and the pH adjusted to 2.0. The ethyl acetate layer was dried and evaporated to yield 550 mg of 2-(3,3-dimethyl 2-oxo-pentanoyl)-2-aza-bicyclo[2.2.1]heptane-3-endo-carboxylic acid as an amorphous solid. Rf(10:1 methylene chloride: methanol)=0.10. Mass spectrum: m/e=266 (P–1). $^{13}$C NMR indicates that 2-(3,3-dimethyl-2-oxo-pentanoyl)-2-aza-bicyclo[2.2.1]heptane-3-endo-carboxylic acid is approximately a 3–1 mixture of rotomers. Principal $^{13}$C NMR peaks (CDCl$_3$; ppm): 206.5, 174.2, 164.1, 61.9, 59.5, 46.8, 39.9, 39.4, 32.2, 29.5, 24.2, 24.1, 23.8, 8.9. $^1$ H NMR (CDCl$_3$) δ 10.75 (brs, 1 H), 3.9–4.3, (m, 2 H), 2.7–2.8 (m, 1 H), 1.4–1.9 (m, 8 H, 0.6–1.2 (m, 9 H).

EXAMPLE 7
2-(3,3-Dimethyl-2-oxo-pentanoyl)-2-aza-bicyclo[2.2.1] heptane-3-exo-carboxylic acid This hydrolysis using the above procedure was complete in 14 hours at room temperature. Rf (10:1 methylene chloride: methanol)=0.10. Mass spectrum: m/e=266 (P–1). $^{13}$C NMR indicates that 2-(3,3-dimethyl-2-oxo-pentanoyl)-2-aza-bicyclo[2.2.1]heptane-3-endo-carboxylic acid is approximately a 3-1 mixture of rotomers. Principal $^{13}$C NMR peaks (CDCl$_3$; ppm): 206.7, 174.0, 162.1 65.2, 59.0, 46.9, 40.9, 35.5, 32.1, 31.1, 27.2, 23.5, 23.0, 8.8. $^1$H NMR (CDCl$_3$) δ 11.4 (brs, 1 H), 3.95 (s, 1 H), 3.92 (s, 1 H), 2.80 (s, 1 H), 1.2–1.8 (m, 8 H), 1.15 (s, 3 H), 1.10 (s, 3 H), 0.7, 0.8 (t, 3 H; rotamers).

EXAMPLE 8
2-(3,3-Dimethyl-2-oxo-pentanoyl)-2-aza-bicyclo[2.2.1] heptane-3-endo-carboxylic acid 3-(3,4,5-trimethoxy-phenyl)-propyl ester A mixture of 0.15 g (0.6) mmol) of 2-(3,3-dimethyl-2-oxo-pentanoyl)-2-aza-bicyclo[2.2.1]heptane-3-endo-carboxylic acid, 0.4 g (1.2 mmol) of dicyclohexylcarbodiimide, 0.4 g (0.7 mmol of 3-(3,4,5-trimethoxyphenyl)-propanol, and 0.85 g (0.7 mmol) of 4-dimethylaminopyridiine dissolved in 5 mL of dichloroethane was stirred for 24 hours at room temperature. The reaction mixture was washed with water, the organic layer dried with anhydrous sodium sulfate, filtered, and evaporated. The residue was chromatographed on silica using 5:1 hexanes:ethyl acetate as the elutant. Appropriate fractions were combined and evaporated to yield 65 mg of residue. This material was purified using a silica preparative thin layer chromatography (TLC) plate (Aldrich) and 2:1 hexanes:ethyl acetate as the elutant to yield 35 mg of 2-(3,3-dimethyl-2-oxo-pentanoyl)-2-aza-bicyclo[2.2.1]heptane-3-endo-carboxylic acid 3-(3,4,5-trimethoxy-phenyl)-propyl ester as an oil. Rf=0.55 (1:1 ethyl acetate:hexanes). Mass Spectrum: m/e=476 (p+1). $^1$H NMR indicates that 2-(3,3-dimethyl-2-oxo-pentanoyl)-2-aza-bicyclo[2.2.1]heptane-3-endo-carboxylic acid 3-(3,4,5-trimethoxy-phenyl)-propyl ester is a mixture of rotomers: $^1$H NMR (CDCl$_3$) δ 6.2 (s,2 H), 4.2, 4.46 (m, 1 H), 4.0–4.2 (m,3 H), 3.7–3.9 (s,s,s,9 H), 2.85 (m, 1 H), 2.6 (t, 2 H), 1.4–2.0 (m, 10 H), 1.10, 1.18, 1.22, 1.3 (s,s,s,s, 6 H), 0.85, 0.75 (t.t, 3 H).

EXAMPLE 9
2-(3,3-Dimethyl-2-oxo-pentanoyl)-2-aza-bicyclo[2.2.1] heptane-3-endo-carboxylic acid 4-phenyl-butyl ester Rf=(2:1 isopropyl ether: hexanes)=0.55. Mass spectrum: m/e=400 (p+1). $^1$H NMR (CDCl$_3$) δ 7.22–7.3 (m,2 H), 7.08–7.2 (m, 3 H), 4.3,4.7 (m, 1 H), 4.0–4.2 (m., 3 H), 2.85 (m, 1 H), 2.6 (t, 2 H), 1.4–1.9 (m, 12 H), 1.05–1.35 (s,s,s,s, 6 H), 0.75–0.85 (t,t, 3 H).

EXAMPLE 10
2-(3,3-Dimethyl-2-oxo-pentanoyl)-2-aza-bicyclo[2.2.1] heptane-3-exo-carboxylic acid 3-(3,4,5-trimethoxy-phenyl)-propyl ester Using 2-(3,3-dimethyl-2-oxo-pentanoyl)-2-aza-bicyclo [2.2.1]heptane-3-exo-carboxylic acid (Example 4B) as the starting material, and following the procedure as outlined in Example 5, 2-(3,3-dimethyl-2-oxo-pentanoyl)-2-aza-bicyclo[2.2.1]heptane-3-exo-carboxylic acid 3-(3,4,5-trimethoxy-phenyl)-propyl ester was isolated as an oil. Rf=0.65 (1:1 ethyl acetate:hexanes). Mass Spectrum: m/e= 476 (p+1). $^1$H NMR indicates that 2-(3,3-Dimethyl-2-oxo-pentanoyl)-2-aza-bicyclo[2.2.1 ]heptane-3-exo-carboxylic acid 3-(3,4,5-trimethoxy-phenyl)-propyl ester is a mixture of rotomers: $^1$H NMR (CDCl$_3$) δ 6.2 (s, 2 H), 4.18, (t, 2 H), 4.1–4.6 (m, 1 H), 3.86 (s, 6 H), 3.82 (s, 3 H), 2.7–2.8 (m, 1 H), 2.62 (t, 2 H), 1.4–2.0 (m, 10 H), 1.1–1.4 (s,s,s,s, 6 H), 0.75, 0.85 (t, 3 H).

EXAMPLE 11
1-(2—Cyclohexylmethanesulfonyl-2-aza-bicyclo[2.2.1]-endo-hept-3-yl)-5-(3,4.5-trimethoxy-phenyl)-pentan-1-one and 1-(2-cyclohexylmethanesulfonyl-2-aza-bicyclo[2.2.1]-exo-hept-3-yl)-5-(3,4,5-trimethoxy-phenyl)-pentan-1-one A. 6-(3,4,5-Trimethoxyphenyl)-2-keto-3-hexenal-diethylacetal A mixture of 6.5 g (16 mmol) of 1,1-diethoxy-3-(triphenylphosphanylidene)-propan-2-one (*Bull. Soc. Chim. Fr.* 1974, 1951–1955) and 3.4 g (15 mmol) of 3,4,5-trimethoxypropionaldehyde (*J. Med. Chem.* 1994, 37, 1660–1669) in 100 ml of toluene was refluxed for 3 hours. The reaction mixture was cooled to room temperature, the solvent evaporated, and the residue chromatographed on 120 g of silica using 4:1 hexane:ethyl acetate as the elutant. Appropriate fractions were combined and evaporated to yield 2 g of 6-(3,4,5-trimethoxyphenyl)-2-keto-3-hexenal-diethylacetal. $^1$H NMR: (CDCl$_3$) δ 7.05 (m, 1 H), 6.42 (m, 1 H), 6.38 (s, 2 H), 4.62 (s, 1 H), 3.80 (s, 6 H), 3.76 (s, 3 H), 3.60 (q, 2 H), 3.50 (q, 2 H), 2.70 (m, 2 H), 2.50 (m, 2 H), 1.18 (t, 6 H).

B. 6-(3,4,5-Trimethoxyphenyl)-2-keto-3-hexanal-diethylacetal

To a solution of 2 g (5.7 mmol) of 6-(3,4,5-trimethoxyphenyl)-2-keto-3-hexenal-diethylacetal in 50 ml of ethanol was added 20 mg of 10% palladium on carbon and the mixture hydrogenated at 50 psi for 8 hours. The catalyst was filtered and the ethanol evaporated to yield 1.8 g of 6-(3,4,5-trimethoxyphenyl)-2-keto-3-hexanal-diethylacetal as an oil. $^1$H NMR (CDCl$_3$) δ 6.38 (s, 2 H), 4.50 (s, 1 H), 3.80 (s, 6 H), 3.76 (s, 3 H), 3.60 (q, 2 H), 3.50 (q, 2 H), 2.50 (m, 4 H), 1.60 (m, 4 H), 1.20 (t, 6 H).

C. 6-(3,4,5-trimethoxyphenyl)-2-keto-hexanal

To a solution 1.8 g of 6-(3,4,5-trimethoxyphenyl)-2-keto-3-hexanal-diethylacetal in 15 ml of THF was added sufficient 6N HCl so that the pH<1. this mixture was refluxed for 18 hours. the mixture was cooled to room temperature and the solvent evaporated. the residue was triturated with 50 ml of ethyl acetate, the ethyl acetate solution dried with sodium sulfate (Na$_2$SO$_4$) and evaporated. the residue was chromatographed on 30 g of silica using CHCl$_3$ as the elutant. Appropriate fractions were combined and evaporated to yield 0.8 g of 6-(3,4,5-trimethoxyphenyl)-2-keto-hexanal as an oil. $^1$H NMR: (CDCl$_3$) δ 9.15 (s, 1 H), 6.40 (s, 2 H), 3.80 (s, 6 H), 3.76 (s, 3 H), 2.50 (m, 4 H), 1.60 (m, 4 H).

D. 1-(2-Aza-bicyclo[2.2.1]hept-5-en-3-yl)-5-(3,4,5-trimethoxy-phenyl)-pentan-1-one (mixture of exo and endo isomers).

A mixture of 0.75 g (2.7 mmol) of 6-(3,4,5-trimethoxyphenyl)-2-keto-hexanal and 0.66 ml (8.0 mmol) of cyclopentadiene in 10 ml of aqueous saturated ammonium chloride was stirred at room temperature for 20 hours. The reaction mixture was diluted with 5 ml of water and extracted with 25 ml of ethyl acetate. The aqueous solution was then adjusted to pH=10 with 1N sodium hydroxide (NaOH) and extracted with ethyl acetate. These ethyl acetate layers were combined, dried (Na$_2$SO$_4$) and evaporated to yield 85 mg of 1-(2-Aza-bicyclo[2.2.1]hept-5-en-3-yl)-5-(3,4,5-trimethoxy-phenyl)-pentan-1-one as a mixture of exo and endo isomers. $^1$H NMR: (CDCl$_3$) δ 6.40 (s, 2 H), 6.22 (m, 1 H), 5.65 (m, 1 H), 3.8 (s, 6 H), 3,75 (s, 3 H), 3.0–4.2 (m, 2 H), 2.5 (m, 5 H), 1.6 (m, 4 H), 1.4 (m, 1 H), 1.2 (m, 1 H). Mass spectrum: m/e=346.2 (p+1).

E. 1-(2-Aza-bicyclo[2.2.1]hept-3-yl)-5-(3,4,5-trimethoxy-phenyl)-pentan-1-one (mixture of exo and endo isomers).

A mixture of 85 mg of 1-(2-Aza-bicyclo[2.2.1]hept-5-en-3-yl)-5-(3,4,5-trimethoxy-phenyl)-pentan-1-one and 50 mg of 10% Pd/C in 10 ml of ethyl acetate was hydrogenated at 50 psi for 6 hours. The reaction mixture was filtered and the solvent evaporated to yield 85 mg of 1-(2-Aza-bicyclo[2.2.1]hept-3-yl)-5-(3,4,5-trimethoxy-phenyl)-pentan-1-one as a mixture of exo and endo isomers. $^1$H NMR: (CDCl$_3$) δ 6.40 (s, 2 H), 3.8 (s, 6 H), 3,75 (s, 3 H), 3.0–4.2 (m, 2 H), 2.5 (m, 5 H), 1.6 (m, 4 H), 1.4 (m, 1 H), 1.2 (m, 1 H). Mass spectrum m/e=348.2 (P+1).

F. 1-(2-Cyclohexylmethanesulfonyl-2-aza-bicyclo[2.2.1]-endo-hept-3-yl)-5-(3,4,5-trimethoxy-phenyl)-pentan-1-one and 1-(2-cyclohexylmethanesulfonyl-2-aza-bicyclo[2.2.1]-exo-hept-3-yl)-5-(3,4,5-trimethoxy-phenyl)-pentan-1-one A mixture of 85 mg (0.24 mmol) of 1-(2-aza-bicyclo[2.2.1]hept-3-yl)-5-(3,4,5-trimethoxy-phenyl)-pentan-1-one (mixture of exo and endo isomers), 70 mg (0.36 mmol) of cyclohexyl-methanesulfonyl chloride (*J.Org.Chem.* 1951; 16 621–624) and 58 mg (0.48 mmol) of 4-dimethylaminopyridine in 10 ml of methylene chloride was stirred at room temperature for 14 hours. The reaction mixture was washed with 1N hydrochloric acid (HCl), dried (Na$_2$SO$_4$), and evaporated. The residue was chromatographed on 20 g of silica using 3:1 hexanes:ethyl acetate as the elutant. Appropriate fractions were combined to yield 4 mg of 1-(2-cyclohexylmethanesulfonyl-2-aza-bicyclo[2.2.1]-exo-hept-3-yl)-5-(3,4,5 -trimethoxy-phenyl)-pentan-1-one (Rf=0.5). $^1$H NMR: (CDCl$_3$) δ 6.40 (s, 2 H), 4.05 (m, 2 H), 3.80 (s, 6 H), 3.75 (s, 3 H), 2.90 (m, 2 H), 2.62 (s, 1 H), 2.50 (m, 4 H), 2.10 (m, 1 H), 1.90 (m, 4 H), 1.60 (m, 15 H), 1.20 (m, 1 H) ) and 10 mg of 1-(2-Cyclohexylmethanesulfonyl-2-aza-bicyclo[2.2.1]-endo-hept-3-yl)-5-(3,4,5-trimethoxy-phenyl)-pentan-1-one (Rf=0.4)$^{13}$C NMR: (CDCl$_3$) δ 6.40 (s, 2 H),4.50 (s, 1 H), 4.20 (s, 1 H), 3.90 (s, 6 H), 3.86 (s, 3 H),2.8–3.1 (m, 3 H), 2.5 (m, 4 H), 1.8–2.0 (m, 4 H), 1.4–1.8 (m, 15 H), 1.1 (m, 2 H)).

EXAMPLE 12

2-(3,3-Dimethyl-2-oxo-butanoyl)-2-aza-bicyclo[2.2.1]heptane-3-endo-carboxylic acid 3-(3,4,5-trimethoxy-phenyl)-propyl ester Substituting tert-butylmagnesium chloride (Aldrich) for 1,1-dimethylpropyl-magnesium chloride in Example 4, 2-(3,3-dimethyl-2-oxo-butanoyl)-2-aza-bicyclo[2.2.1]heptane-3-endo-carboxylic acid 3-(3,4,5-trimethoxy-phenyl)-propyl ester can be prepared using the described sequence. Rf=0.65 (1:1 ethyl acetate:hexanes). Mass Spectrum: m/e=462.2 (p+1). $^1$H NMR: (CDCl$_3$) δ 6.38 (s, 2 H), 4.3, 4.7 (m, 1 H), 4.15 (t, 2 H), 4.05 (s, 1 H), 3.8 (s, 6 H), 3.78 (s, 3 H), 2.82 (m, 2 H), 2.6 (t,2 H), 1.8–2.0 (m, 3 H), 1.6–1.7 (m, 2 H), 1.4–1.6 (m, 3 H), 1.22 (s, 9 H).

EXAMPLE 13

1-(2-(Chloro-quinolin-3-ylmethyl)-pyrrolidin-3S-ylamine

A mixture of 1 g (5.4 mmol) of 3S-(+)-t-butoxycarbonylaminopyrrolidine, 1.1 g (6 mmol) of 2-chloroquinoline-3-carboxaldehyde (*J. Chem. Soc. Perkin Trans.*1, 1981, 1520–1530) and 2.3 g of sodium traicetoxyborohydride in 20 ml methylene chloride was stirred at room temperature (rt) for 18 hours. To this mixture was added 5 ml of water and the reaction was stirred for an additional 1 hour. The organic layer was then separated from the water layer, washed with 10 ml of saturated sodium bicarbonate, dried (Na$_2$SO$_4$) and evaporated. The residue was chromatographed on 40 g of silica using 1:1 ethyl acetate:chloroform (EtOAc:CHCl$_3$) as the elutant. Appropriate fractions were combined and evaporated to yield 1-2-Chloro-quinolin-3-ylmethyl)-pyrrolidin-3-yl]-carbamic acid tert-butyl ester as an oil. $^1$H NMR: (CDCl$_3$) δ 8.10 (s, 1 H, 7.80 (d, 1 H), 7.70 (t, 1 H), 7.50 (t, 1 H), 4.82 (s, 1 H), 4.20 (br s, 1 H), 3.80 (s, 2 H), 2.90 (m, 1 H), 2.74 (m, 1 H), 2.65 (m, 1 H), 2.48 (m, 1 H), 2.30 (m, 1 H), 1.68 9 m, 1 H), 1.35 (s, 9 H). This material was dissolved in 25 ml of CHCl$_3$ and the solution was saturated with HCl gas. After standing 18 hours at room temperature (rt) the mixture was filtered. The precipitate was triturated with isopropyl ether, collected and dried to yield 1.5 g of 1-(2-Chloro-quinolin-3-ylmethyl)-pyrrolidin-3S-ylamine dihydrochloride salt. Mass spectrum: m/e=262,264 (P+1: P+3).

EXAMPLE 14

1-(1H-Indol-3-ylmethyl)-pyrrolidin-3-ylamine hydrochloride

Prepared from indole-3-carboxaldehyde (Aldrich Chemical Company) and 3S-(+)-t-butoxycarbonylaminopyrrolidine, using a procedure similar to that of Example 13. Mass spectrum: m/e=177 (P+1).

EXAMPLE 15

1-Pyridin-3-ylmethyl-pyrrolidin-3-ylamine hydrochloride

Prepared from pyridine-3 carboxaldehyde (Aldrich Chemical Company) and 3S-(+)-t-butoxycarbonylaminopyrrolidine, using a procedure similar to that of Example 13. Mass spectrum: m/e=177(P+1).

EXAMPLE 16
2-Aza-bicyclo[2.2.1]heptane-3-endo-carboxylic acid ethyl ester

A mixture of 28 g (0.16 m) of exo and endo-2-azabicyclo[2.2.1]hept-5-ene-3-carboxylic acid ethyl esters (Example 1) and 18.5 g (0.18 m) of benzaldehyde in 300 ml of methylene chloride was cooled to 15° C. and stirred for 15 minutes. To this solution was added portionwise 78 g (0.38 m) of sodium triacetoxyborohydride over a 1 hour period, maintaining the reaction temperature at 15° C. After the addition mixture was cooled to 10° C. and quenched with the slow addition of 100 ml of water. The pH of the reaction mixture was adjusted to 8.0 with 25% aqueous NaOH. The organic layer was separated from the water layer, dried and evaporated. The residue was chromatographed on 800 g of silica using 10:1 hexanes:ethyl acetate as the elutant. Appropriate fractions were combined to yield 24 g of 2-benzyl-2-aza-bicyclo[2.2.1]hept-5-ene-3-endo-carboxylic acid ethyl este. This matetial was dissolved in 200 ml of ethyl acetate and to this solution was added 300 mg of 10% Pd/C. The mixture was hydrogenated at 50 psi for 18 hours. The mixture was filtered and evaporated. A $^1$H NHR of the oil indicated that benzyl alcohol was present as an impurity. Therefore, the oil was mixed with 200 ml of water and the pH adjusted to 3.0 with 6N HCl. Extraction with ethyl acetate (3×25 ml) removed the benzyl alcohol impurity. The pH of the aqueous layer was adjusted to 10 with $^1$N NaOH and extracted with ethyl acetate. The ethyl acetate extracts were combined, dried (Na$_2$So$_4$) and evaporated to yield 10 g of 2-aza-bicyclo[2.2.1]heptane-3-endo-carboxylic acid ethyl ester as an oil. $^1$H NMR: (CDCl$_3$) δ4.15 (q,2 H), 3.72 (s 1 H), 3.40 (s, 1 H), 2.55 (s, 1 H), 1.70 (m, 2 H), 1.3–1.6 (m, 5 H), 1.15 (m, 4 H). Mass spectrum: m/e=170.2 (p+1).

EXAMPLE 17
2-Cyclohexylmethanesulfonyl2-aza-bicyclo[2.2.1]heptane-3-endo-carboxylic acid ethyl ester A solution of 0.8 g (4.7 mmol) of 2-aza-bicyclo[2.2.1]heptane-3-endo-carboxylic acid ethyl ester, 1.0 g (5.0 mmol) of cyclohexyl-methanesulfonyl chloride (J. Org. Chem. 1951; 16 621–624) and 0.9 g (7.5 mmol) of 4-dimethylaminopyridine in 20 ml of methylene chloride was stirred at room temperature for 48 hours. The reaction was diluted with 10 ml of water and the pH adjusted to 3.0 with 1N HCl. The methylene chloride layer was separated from the aqueous layer, dried (Na$_2$SO$_4$) and evaporated to yield 1.3 g of 2-cyclohexylmethane-sulfonyl-2-aza-bicyclo[2.2.1]heptane-3-endo-carboxylic acid ethyl ester as an oil. $^1$H NMR: (CDCl$_3$) δ 4.42 (s, 1 H), 4.2 (s, 1 H), 4.15 (q, 2 H), 3.05 (m, 1 H), 3.8–3.95 (m, 2 H), 1.8–2.0 (m, 3 H), 1.4–1.8 (m, 9 H), 1.2–1.4 (m, 2 H), 1.2 (t, 3 H), 1.0–1.2 (m, 3 H). Mass spectrum: m/e=330 (p+1).

EXAMPLE 18
2-Cyclohexylmethanesulfonyl-2-aza-bicyclo[2.2.1]heptane-3-endo-carboxylic acid A solution of 0.75 g (2.3 mmol) of 2-cyclohexylmethane-sulfonyl-2-aza-bicyclo[2.2.1]-heptane-3-endo-carboxylic acid ethyl ester in a mixture of 10 ml of dioxane and 3 ml of 6N HCl was heated to 90° C. for 18 hours. The reaction was cooled to rt and the solvent evaporated. The residue was mixed with 10 ml of water, the pH adjusted to 9.5 (1N NaOH), and mixture extracted with ethyl acetate. The pH of the water layer was then adjusted to 2.0 with 1N HCl and extracted with ethyl acetate. The pH=2 ethyl acetate extracts were combined, dried (Na$_2$SO$_4$) and evaporate to yield 350 mg of 2-cyclohexymethane-sulfonyl-2-aza-bicyclo[2.2.1]heptane-3-endo-carboxylic acid as an oil. $^1$H NMR:(CDCl$_3$) δ 4.55 (s, 1 H), 4.22 (s, 1 H), 2.8–3.0 (m, 3 H), 1.8–2.1 (m, 3 H), 1.4–1.8 (m, 9 H), 1.2–1.4 (m, 2 H), 1.0–1.2 (m, 3 H). Mass spectrum: m/e=301.2 (p–1).

EXAMPLE 19
2-Cyclohexylmethanesulfonyl-2-aza-bicyclo[2.2.1]heptane-3-carboxylic acid[1-(2-chloro-quinolin-3-ylmethyl)-pyrrolidin-3-yl]-amide.

A mixture of 0.28 g (0.9 mmol) of 2-cyclohexymethane-sulfonyl-2-aza-bicyclo[2.2.1]heptane-3-endo-carboxylic acid, 0.4 ml (3.3 mmol) TEA, 0.35 g (1.8 mmol) 1-(3-dimethylaminopropyl)-3-ethylcarbodiimide hydrochloride (Aldrich Chemical Co.), 10 mg of 4-dimethylaminopyridine, and 0.4 g (1.1 mmol) of 1-(2-chloro-quinolin-3-ylmethyl)-pyrrolidin-3S-ylamine dihydrochloride in 20 ml of methylene chloride was stirred for 18 hours at room temperature. The solvent was evaporated and the residue was chromatographed on 20 g of silica using 5:1 CHCl$_3$:ethylacetate as the elutant. Appropriate fractions were combined and evaporated to yield 50 mg of 2-cyclohexylmethanesulfonyl-2-aza-bicyclo[2.2.1]heptane-3-carboxylic acid [1-(2-chloro-quinolin-3-ylmethyl)-pyrrolidin-3-yl]-amide as amorphous solid.
$^1$H NMR: (CDCl$_3$) δ 8.35 (s, 1 H), 7.95 (m, 2 H), 7.65 (m, 1 H) 7.50 (m, 1 H), 7.15 (m, 1 H), 4.6 (m, 1 H), 4.21 (m, 1 H), 3.7–4.0 (m, 3 H), 2.9–3.1 (m, 2 H), 2.6–2.9 (m, 3 H), 2.15–2.6 (m, 3 H), 1.9–2.2 (m, 3 H), 1.4–1.9 (m, 9 H), 1.0–1.4 (m, 6 H). Mass spectrum: m/e=545,547 (P+1; p=3), TLC (10:1, EtOAc:CHCl$_3$), Rf=0.6.

EXAMPLE 20
2-Cyclohexylmethanesulfonyl-2-aza-bicyclo[2.2.1]heptane-3-carboxylic acid[1-(1H -indol-3-ylmethyl)-pyrrolidin-3-yl]-amide.
$^1$H NMR: (CDCl$_3$) δ 8.35 (s, 1 H) 7.68 (m, 1 H), 7.0–7.4 (m, 5 H) 4.50 (br s, 1 H), 3.6–4.2 (m, 4 H), 2.4–3.1 (m, 5 H), 0.6–2.4 (m, 20 H). Mass Spectrum: m/e=499.1(P+1). TLC (10:1 CHCl$_3$:CH$_3$OH), Rf=0.3.

EXAMPLE 21
2-Cyclohexylmethanesulfonyl-2-aza-bicyclo[2.2.1]heptane-3-carboxylic acid (1-pyridinl-3-ylmethyl-pyrrolidin-3-yl)-amide.
$^1$H NMR: (CDCl$_3$) δ 8.3\45 (m, 2 H), 7.65 (m, 1 H), 7.2 (m, 1 H) 7.0 (m, 1 H), 4.50 (m, 1 H), 4.20 (m, 1 H), 4.0 (s, 1 H) 3.60 (m, 2 H), 2.0–3.1 (m, 6 H) 1.6–2.0 (m, 2 H), 1.0–1.8 (m, 18 H). Mass Spectrum: m/e=461.3(P+1). TLC (10:1, CHCl$_3$:CH$_3$OH), Rf=0.25.

What is claimed is:

1. A compound of the formula

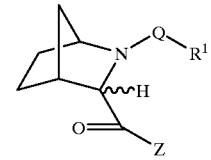

(I)

wherein Q is —S(=O)$_2$—, —C(=O)—N(H)—, —C(=O)—CH$_2$—, —CH$_2$C(=O)—, —C(=O)—C(=O)—, —C(=S)—C(=O)— or —C(=O)—CH(OH)—;

R$^1$ is phenyl, phenyl-(C$_1$–C$_3$)alkyl or (C$_1$–C$_6$)alkyl, and wherein the cyclic and (C$_1$–C$_6$)alkyl moieties of R$^1$ may optionally be substituted with from zero to three substituents that are selected, independently, from hydroxy, formate, acetate, $(C_1-C_4)$alkyl, nitro, cyano, halo and $NR^4R^5$ wherein $R^4$ and $R^5$ are selected, independently, from hydrogen and $(C_1-C_4)$alkyl;

Z is —$XCHR^2R^3$ or —$CHR^9R^{10}$;

X is oxygen or $NR^8$ wherein $R^8$ is hydrogen or $(C_1-C_6)$ alkyl;

$R^2$ and $R^3$ are selected, independently, from hydrogen, $(C_1-C_{12})$ straight or branched alkyl, $(C_5-C_8)$ cycloalkyl,$(C_5-C_8)$cycloalkyl-$(C_1-C_{12})$ straight or branched alkyl, aryl, aryl-$(C_1-C_{12})$straight or branched alkyl, wherein said aryl is selected from phenyl-naphthyl, and 2-naphthyl, heteroaryl and heteroaryl-$(C_1-C_{12})$ straight or branched alkyl, wherein said heteroaryl is selected from, 2-furyl, 3-furyl, 2-thienyl, 2-pyridyl, 3-pyridyl and 4-pyridyl, and wherein one or two of the $CH_2$ moieties of said phenyl-$(C_1-C_{12})$alkyl, $(C_5-C_8)$cycloalkyl-$(C_1-C_{12})$ straight or branched alkyl or heteroaryl-$(C_1-C_{12})$ straight or branched alkyl may optionally and independently be replaced with NH or C=O, and wherein each of the cyclic and acyclic moieties of $R^2$ and $R^3$ may optionally be substituted with from zero to three substituents that are selected, independently, from halo, hydroxy, cyano, nitro, trifluoromethyl, $NR^6R^7$ wherein $R^6$ and $R^7$ are defined as $R^4$ and $R^5$ above, $(C_1-C_4)$alkyl, $(C_1-C_4)$alkoxy, phenoxy and benzyloxy;

or $R^2$ and $R^3$ together with the carbon to which they are attached, from a group of the formula

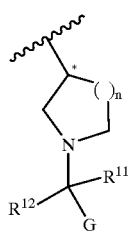

(A)

wherein n is one or two, $R^{11}$ and $R^{12}$ are selected, independently, from hydrogen, $(C_{10}-C_6)$alkyl and fluorine, or together form an oxo (=O) group, and G is selected form four to seven membered monocyclic, or ten to fourteen membered bicyclic carbocyclic rings that can be saturated or unsaturated, wherein from one to three of the nonfused carbon atoms of said monocyclic rings, and from one to five of the carbon atoms of said bicyclic rings that are not part of the benzo ring shown in formula I, may optionally and independently be replaced by nitrogen, oxygen or sulfur, and wherein said monocyclic and bicyclic rings may optionally be substituted with one or more substituents, wherein said substituents are selected, independently, from $(C_1-C_6)$ alkyl optionally substituted with from one to seven fluorine atoms, $(C_1-C_6)$ alkoxy optionally substituted with from one to seven fluorine atoms, nitro, cyano, halo, amino, $(C_1-C_6)$alkylamino and $[(C_1-C_6)$ alkyl$]_2$amino; and $R^9$ and $R^{10}$ are defined as $R^2$ and $R^3$ are defined above;

with the proviso that $R^2$ and $R^3$ cannot both be hydrogen, and $R^9$ and $R^{10}$ cannot both be hydrogen;

or a pharmaceutically acceptable salt thereof.

2. A compound according to claim 1 wherein Z is —$XCR^2R^3$ and X is oxygen.

3. A compound according to claim 1 wherein Z is —$XCR^2R^3$ and X is $NR^8$.

4. A compound according to claim 1 wherein none of the alkyl moieties of $R^1$, $R^2$, $R^3$, $R^9$ and $R^{10}$ groups are substituted.

5. A compound according to claim 1 wherein Q is —$S(=O)_2$—.

6. A compound according to claim 1 wherein Q is —$C(=O)$—$CH_2$—.

7. A compound according to claim 1 wherein Q is —$CH_2$—$C(=)$—.

8. A compound according to claim 1 wherein Q is —$C(=O)$—$C(=O)$—.

9. A compound according to claim 1 wherein Q is —$C(=O)$—$CH(OH)$—.

10. A compound according to claim 1 wherein Q is —$C(=O)$—$N(H)$—.

11. A compound according to claim 1 wherein Q is —$C(=S)$—$C(=O)$—.

12. A compound according to claim 1 wherein Z is —$CHR^9R^{10}$.

13. A compound according to claim 1, wherein one of $R^2$ and $R^3$, if Z is —$XCHR^2R^3$, or one of $R^9$ and $R^{10}$, if Z is —$CHR^9R^{10}$, is hydrogen and the other is selected from $(C_1-C_{12})$ straight or branched alkyl, $(C_5-C_8)$cycloalkyl, $(C_5-C_8)$cycloalkyl-$(C_1-C_{12})$ straight or branched alkyl, phenyl and phenyl-$(C_1-C_{12})$straight or branched alkyl.

14. A pharmaceutical composition for the treatment of a disorder the treatment or prevention of which can be effected or facilitated by inhibiting the rotomase activity of FKBP-12 in a mammal, including a human, comprising an amount of a compound according to claim 1 that is effective in the treatment of such disorder, and a pharmaceutically acceptable carrier.

15. A method for the treatment of a disorder the treatment or prevention of which can be effected or facilitated by inhibiting the rotomase activity of FKBP-12 in a mammal, including a human, comprising administering to a subject in need of said treatment an amount according to claim 1 that is effective in treating such disorder.

16. A pharmaceutical composition for the treatment of a disorder in a mammal that is a neurodegenerative disease or other disorder involving nerve damage comprising an amount of a compound according to claim 1 that is effective in the treatment of such disorder, and a pharmaceutically acceptable carrier.

17. A method for the treatment of disorder in a mammal that is a neurodegenerative disease or other disorder involving nerve damage comprising administering to a subject in need of said treatment an amount of a compound according to claim 1 that is effective in treating such disorder.

18. A pharmaceutical composition according to claim 16, wherein said neurodegenerative disease or other disorder involving nerve damage is selected from the group consisting of Alzheimer's disease, Parkinson's disease, ALS, Huntington's disease, senile dementia of the Alzheimer's type, AIDS related neuropathies, multiple sclerosis, brain damage associated with stroke or head trauma, all forms of degenerative disease affecting the central or peripheral nervous system, cerebellar-brainstem atrophies, syndromes of progressive ataxias, all forms of muscular dystrophy, progressive muscular atrophies, progressive bulbar muscular atrophy, physical or traumatic damage to the central or peripheral nervous system, herniated, ruptured or prolapsed intervertebrae disc syndromes, cervical spondylosis, plexus disorders, thoracic outlet syndromes, all forms of peripheral neuropathy, trigeminal neuralgia, glossopharyngeal neuralgia, Bell's Palsy, all forms of auto-immune related disease resulting in damage to the central or peripheral nervous system, multiple sclerosis, myasthenia gravis, Guillain-Barré syndrome, dapsone ticks, bulbar and retrobulbar affections of the optic nerve, retinopathies, retrobulbar neuritis, prion diseases, hearing disorders and tinnitus.

19. A method according lo claim 17, wherein said neurodegenerative diseases or other disorder involving nerve damage is selected from the group consisting of Alzheimer's disease, Parkinson's disease, ALS, Huntington's disease, senile dementia of the Alzheimer's type, AIDS related neuropathies, multiple sclerosis, brain damage associated with stroke or head trauma, all forms of degenerative disease affecting the central or peripheral nervous system, cerebellar-brainstem atrophies, syndromes of progressive ataxias, all forms of muscular dystrophy, progressive muscular atrophies, progressive bulbar muscular atrophy, physical or traumatic damage to the central or peripheral nervous system, herniated, ruptured or prolapsed intervertebrae disc syndromes, cervical spondylosis, plexus disorders, thoracic outlet syndromes, all forms of peripheral neuropathy, trigeminal neuralgia, glossopharyngeal neuralgia Bell's Palsy, all forms of auto-immune related disease resulting in damage to the central or peripheral nervous system, multiple sclerosis, myasthenia gravis, Guillain-Barré syndrome, dapsone ticks, bulbar and retrobulbar affections of the optic nerve, retinopathies, retrobulbar neuritis, prion diseases, hearing disorders and tinnitus.

* * * * *